United States Patent [19]

Koike et al.

[11] Patent Number: 4,679,437

[45] Date of Patent: Jul. 14, 1987

[54] METHOD OF DETECTING FLAWS IN THICK WALL STEEL PIPE WITH ULTRASONIC ANGLE BEAM TECHNIQUE

[75] Inventors: Mitsuhiro Koike; Nobuaki Yakoh, both of Kanagawa, Japan

[73] Assignee: Mitsubishi Denki Kabushiki Kaisha, Japan

[21] Appl. No.: 784,081

[22] Filed: Oct. 4, 1985

[30] Foreign Application Priority Data

Oct. 4, 1984 [JP] Japan .................................. 59-208806

[51] Int. Cl.4 ............................................. G01N 29/04
[52] U.S. Cl. ........................................ 73/622; 73/637; 73/638
[58] Field of Search ................... 73/622, 633, 637, 638

[56] References Cited

U.S. PATENT DOCUMENTS

| | | | |
|---|---|---|---|
| 3,302,453 | 2/1967 | Wood et al. | 73/622 |
| 3,552,190 | 1/1971 | Lefebvre | 73/638 |
| 4,434,660 | 3/1984 | Michalls | 73/638 |

Primary Examiner—Howard A. Birmiel
Attorney, Agent, or Firm—Sughrue, Mion, Zinn, Macpeak, and Seas

[57] ABSTRACT

A method of reliably detecting flaws in a thick wall steel pipe with an ultrasonic beam in which flaws of the internal surface of the pipe are detected using a shear wave mode. The transmitting probe is disposed slantingly relative to both the longitudinal and transverse directions of the pipe so that the shear wave emitted therefrom is incident onto the pipe at a refraction angle of 35 to 70 degrees, whereby the beam inside the walls of the pipe is made to impinge on surface flaws of the inner surface of the pipe at an angle in the same range.

6 Claims, 8 Drawing Figures

$\gamma_t = \theta_t + \beta$

$2 \sin \alpha_t = 2\Delta L / D$

METHOD OF DETECTING FLAWS IN THICK WALL STEEL PIPE WITH ULTRASONIC ANGLE BEAM TECHNIQUE

BACKGROUND OF THE INVENTION

The present invention relates to a method of detecting flaws in a thick wall steel pipe with an ultrasonic angle beam technique.

As is well known, ultrasonic waves used for detecting flaws in metal materials include a compression wave mode and a shear wave mode. A method of detecting flaws with an ultrasonic angle beam technique of shear wave mode, for example, as specified in G-0582 and Z-2344 of JIS (Japanese Industrial Standards), has been widely used to detect flaws in steel pipes.

The refraction angle of an angle probe is determined in accordance with the ratio of the wall thickness (t) to the outer diameter (D) of the pipe (hereinafter, called as t/D). However, in the case of a thick wall steel pipes having ratio t/D of 20% or more, it is difficult to detect a longitudinal flaw (a slit-like flaw parallel to the longitudinal axis of a test material) on inner surface stably by such an ultrasonic angle beam technique since the injection angle of ultrasonic wave on outer surface of pipe exceeds the critical angle related to the shear wave mode in accordance with The Law of refraction of ultrasonic wave. (This Law has been well known as Snell's Law) and the refracted shear wave does not reach the inner surface of the pipe. This phenomenon is described in "Method of Ultrasonic Examination" (revised new edition), The Nikkan Kogyo Shimbun, Co., Ltd., pages 490–493, (July 30, 1974); and "Ultrasonic Testing Method A", Japanese Society on Non-Destructive Inspection, pages 231–244, (May 1, 1974).

Various methods have been proposed for detecting a longitudinal flaw on the inner-surface of thick wall steel pipes having ratio t/D of more than 20% in the past.

Figure 1:
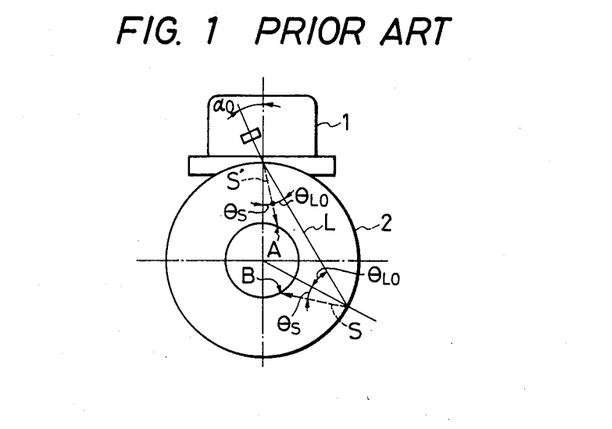
FIG. 1 is a diagram illustrating the principles of a conventional ultrasonic testing method for detecting a longitudinal flaw on inner surface of thick wall steel pipes.
Figure 2:
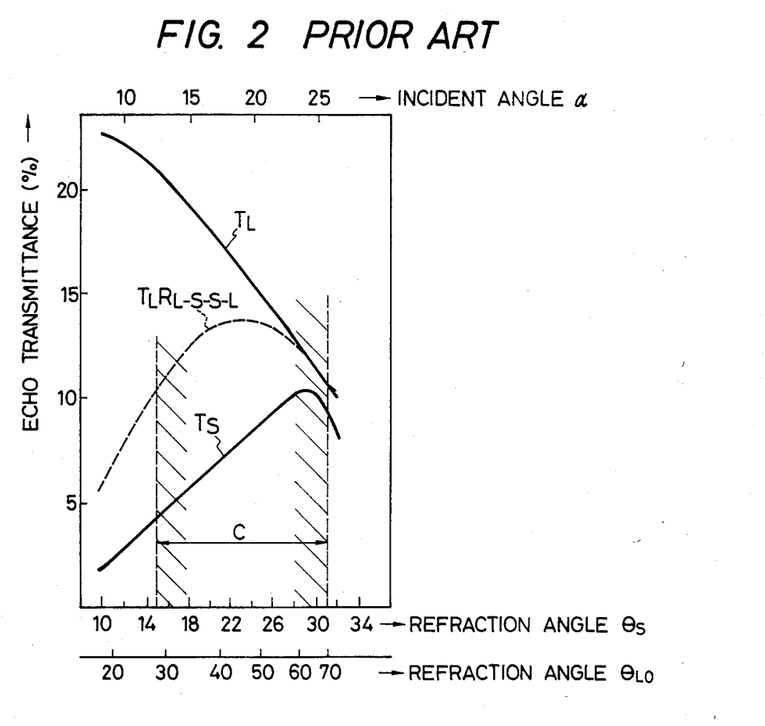
FIG. 2 is a graph showing the echo transmittance of ultrasonic waves and the refraction angle in the conventional method.

FIG. 1 is an explanatory diagram illustrating a method of detecting longitudinal flaws on the inner surface of such a thick wall steel pipe. FIG. 2 is a diagram showing echo transmittance and the refraction angle of the ultrasonic waves for detecting a longitudinal flaw on inner surface of a thick wall steel pipe. Such a technique is disclosed, for example, in Japanese Patent Publication No. 17024/1981.

In FIG. 1, reference numeral 1 designates a transmitting/receiving probe for detecting a longitudinal flaw on inner surface and 2 a steel pipe to be tested having a large ratio of t/D.

In the conventional method, an ultrasonic beam injected into the steel pipe 2 (test material) at an incidence angle $\alpha_o$ in the circumferential direction from the probe 1 generates a compression wave L at a refraction angle $\theta_{Lo}$ and a shear wave S' at a refraction angle $\theta_S$. The compression wave L, reflected by the outer wall of test material generates a shear wave S by mode conversion. The shear wave S reaches a point B on the inner surface of the test material at a refraction angle $\theta_S$.

If there is a longitudinal flaw at the point B, the shear wave echo signal (shear wave mode) of the flaw travels along the same path in the reverse order of the incident wave and is mode-converted into a compression wave by refraction at the outer wall, which returns to the incident point and is received by the probe 1 as a flaw echo.

The shear wave S' at the refraction angle $\theta_S$ generated at the same time as the compression wave reaches a point A, and if there is a flaw, the wave S' returns to the probe 1 along the reverse route as a flaw echo.

In FIG. 2, $T_L$ designates a curve showing the echo transmittance of the compression wave L as a function of the incidence angle and the refraction angle $\theta_{Lo}$, C an effective flaw detecting region in the method of FIG. 1 and $T_S$ a curve showing the echo transmittance of the shear wave S' generated directly at the incident point as a function of the incidence angle and the refraction angle $\theta_S$. The echo transmittance of waves passing along the route, in the order of the compression wave L → the shear wave S → the flaw, indicated by ($T_L R_L$-S-S-L), shows that the sensitivity for detecting longitudinal flaw on inner surface of the test material is improved.

It can be said that the echo transmittance is improved with this method; however, it is also a fact that the echo transmittance is less than in the case of a shear wave refraction angle within a range of 35 to 70 degrees.

Further, because the allowable range of the refraction angle used for detecting longitudinal flaws is narrow, that is, only from 15 to 31 degrees, the range of allowable incidence angles of the ultrasonic beam onto the test material is also very narrow, that is, only from about 7 to 14 degrees, for example, in the widely used immersion method. Therefore, it is difficult to automate the testing with this method, because it is difficult to keep the accurate probe position of the testing mechanism during actual operation.

Steel pipes for a boiler or a heat exchanger, which are the main objects of applications of these methods, are rolled during manufacture, their reduction ratio is relatively small, and hence the degree of deformation in the outer and inner diameters is generally large and the pipe surfaces are generally rough. Accordingly, for inspection of such steel pipes, it is difficult to employ the above mentioned method of a longitudinal flaw detection in which flaws are detected with mode conversion by reflecting an ultrasonic beam at the outer wall of the test material because the reproductivity of flaw detection is extremely low due to scattering of the ultrasonic beam by the rough outer surface.

Moreover, if a material which has been worked is subject to flaw detection, the energy losses tend to be quite large. Accordingly, it has been strongly desired to develop a flaw detecting method which is capable of performing inspection before working on the material.

SUMMARY OF THE INVENTION

The present invention has been attained in order to solve the problems discussed above, and is directed to the provision of a method in which a shear wave of an ultrasonic beam is made incident on the inner surface of a test material in such a manner as to provide a high conversion efficiency and without the ultrasonic beam being reflected from the outer wall of the test material.

According to the inventive ultrasonic flaw detecting method, there is hardly any effect due to deformations in the outer and inner diameters or roughness of the surface of test material. Also, it is possible to apply the inventive method of flaw detection to steel pipes for a boiler, a heat exchanger, etc. having surface as rolled.

More specifically, in the method of detecting longitudinal flaws in a thick wall steel pipes with an ultrasonic angle beam technique according to the present invention, the incidence angle of the ultrasonic beam from a transmitting probe onto the test material is selected such that the shear wave refraction angle $\theta_S$ is within a range of 35 to 70 degrees, for which the echo transmittance is better. Hence, the shear wave incidence angle onto longitudinal flaws on the inner surface of the test material is within the range of 35 to 70 degrees, for which echo transmittance is better. Accordingly, the probe is disposed slantingly relative on the axial and circumferential directions of the test material, and longitudinal flaw detection on inner surface is performed by disposing geometrically the receiving probe at a position where the ultrasonic beam reflected from the flaw reaches the outer surface of the pipe. The echo signal does not return to the transmitting probe in case of a longitudinal flaw on the inner surface.

According to the present invention, with the incidence angle from the probe relative to a steel pipe and the incidence angle relative to a flaw in the inner surface of the pipe established as described above, that is, with the refraction angle and the incidence angle to the flaw being within a range of 35 to 70 degrees, optimized flaw detection is achieved because an axial incidence angle is provided in addition to the circumferential incident angle, differing from the conventional method in which only a circumferential incidence angle is employed.

Further, because it is unnecessary to employ for echo signal reflected from the outer wall of the test material, the results of flaw detection is affected very little by deformations in the outer and inner diameters and/or a roughness of the outer surface of the test material, whereby it is made possible to achieve highly reliable ultrasonic flaw detection in the case of a longitudinal flaw on an inner surface, even for steel pipes manufactured by rolling, and particularly for pipes for a boiler or heat exchanger.

Moreover, if the test material is inspected along the circumferential direction using a slantingly disposed probe having a refraction angle equal to the incidence angle onto the longitudinal flaw on the inner surface, the ultrasonic beam will be incident onto a flaw on the outer surface of the pipe with an incidence angle equal to the refraction angle, and hence it becomes possible to detect longitudinal flaws of both the inner and outer surfaces of the test material with a better signal to noise ratio and with the same sensitivity or flaw detectability.

Another example of an ultrasonic testing method is described in: Josef and Herbert Krautkraemer, "Ultrasonic Testing of Materials", pages 378 to 381 of the Japanese text. In accordance with the method therein described, compression waves are employed to detect flaws in a thick wall member. Various types of flaw detection methods are described for sensing faults in tubular members in which two detecting devices separated axially from one another and a partition wall are employed. However, the disclosed methods are not suitable for detecting flaws occurring within a thick-walled tubular member.

In the article "Ultrasonic Testing Method B", Japanese Society on Non-destructive Inspection (1979), pages 207 and 208, a method is described for detecting flaws on the inner surface of thick wall steel pipes using mode conversion between compression and shear waves. This technique is essentially the same as that taught by Japanese Patent Publication No. 17024/1981 discussed above.

DESCRIPTION OF THE PREFERRED EMBODIMENT

Figure 3:
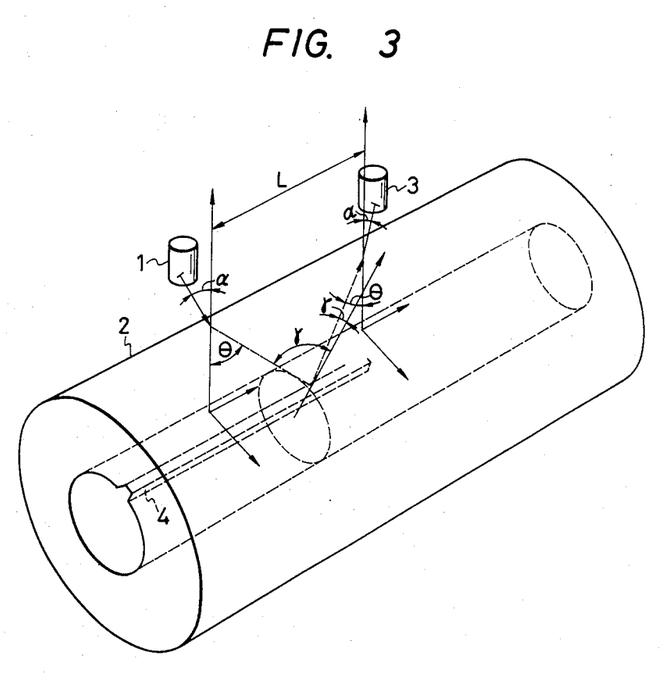
FIG. 3 is a schematic view illustrating a flaw detecting method according to the present invention.

FIG. 3 is an explanatory diagram of the present invention, in which reference numeral 1 designates an ultrasonic transmitting probe test material 2 (steel pipes), an ultrasonic probe 3 for receiving echoes from flaws of the inner surface of a test material, a flaw 40n the inner surface, $\alpha$ the incidence angle of ultrasonic waves incident on the test material from the probe 1, $\theta$ the refraction angle in the test material, $\gamma$ the incidence angle of ultrasonic waves incident on the inner surface flaw 4, and L is the distance between probe index of probes 1 and 3.

Figure 4:
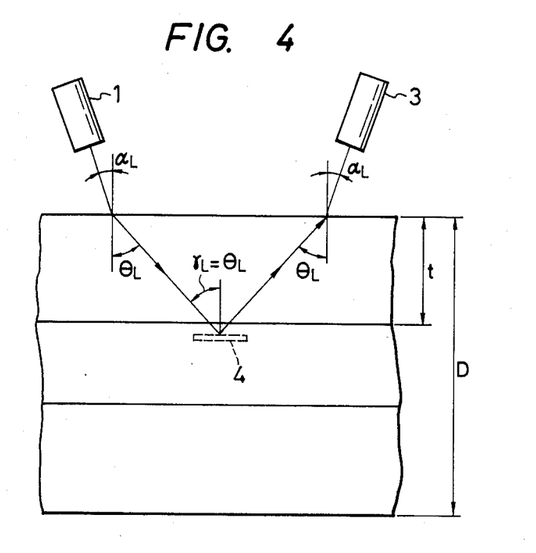
FIG. 4 is a schematic view showing ultrasonic beam paths transmission in the method of the invention viewed in the axial direction of a test material.

FIG. 4 is a schematic view showing the paths of the ultrasonic waves viewed in the axial direction of the pipe, in which reference character D designates the outer diameter of the test material 2, t is the wall thickness of the same, $\alpha_L$ the incidence angle viewed in the axial direction of the beam incident on the test material 2, $\theta_L$ the refraction angle in the test material viewed in the axial direction thereof, and $\gamma_L$ the incidence angle of the ultrasonic waves on the inner surface flaw 4 viewed in the axial direction.

Figure 5:
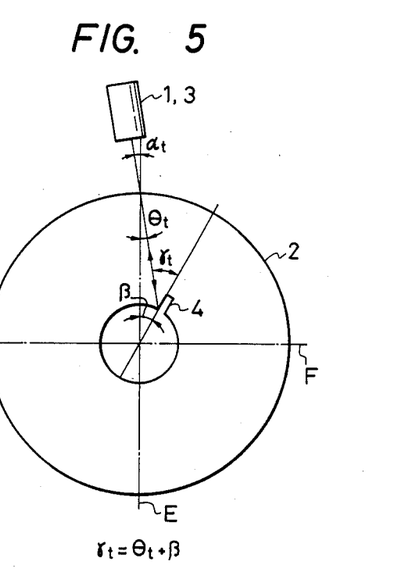
FIG. 5 is a schematic view showing the paths of ultraonsic beam transmission viewed in the circumferential direction of pipe.

FIG. 5 is a schematic view showing the paths of ultrasonic wave transmission viewed in the circumferential direction of the pipe, in which reference characters E and F designate center lines of the test material 2, $\alpha_t$ the incidence angle viewed in the circumferential direction of the ultrasonic beam incident on the test material 2 from the probe 1, $\theta_t$ the refraction angle in the test material viewed in the transverse direction, $\gamma_t$ the incidence angle of the ultrasonic wave beam into the inner surface flaw 4 viewed in the transverse direction, $\beta$ an angle defined geometrically by the position where the ultrasonic beam is incident on the inner surface flaw 4, and a center line E and a center point of the test material 2, the angle $\beta$ hereinafter being referred to as an "incremental interior angle".

Figure 6:
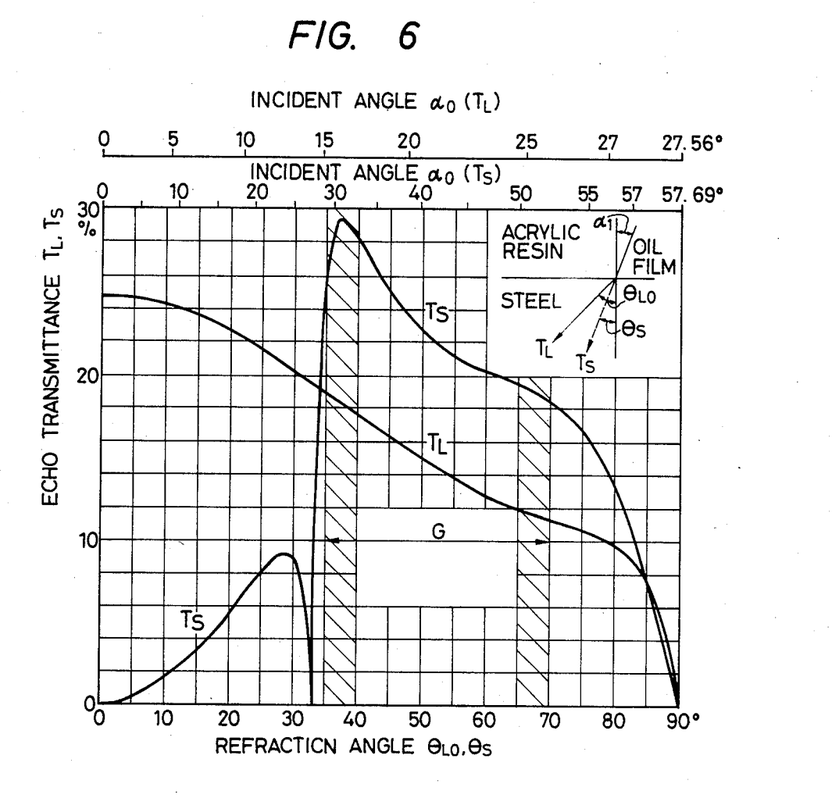
FIG. 6 shows a graph indicating the echo transmittance of the ultrasonic waves as a function of the refraction angle of ultrasonic share waves.

FIG. 6 is a graph showing the relationship between the echo transmittance and the refraction angle in acryl which is a material of attachment and steel (the materials of the pipe), in which reference symbol $T_S$ designates the echo transmittance of shear wave, $T_L$ the echo transmittance of compression wave, $\alpha_O(T_L)$ the incidence angle of compression wave, $\alpha_O(T_S)$ the incidence angle of share waves, $\theta_{LO}$ the refraction angle of compression wave, $\theta_S$ the refraction angle of share waves, and G an effective range of this invention.

A shear wave with a refraction angle within a wide range (35 to 75 degrees) where the echo transmittance is high for the shear wave, indicated by the effective range G in FIG. 6, has been considered to be impossible for use of inner surface flaw detection for thick wall steel pipes having a large value of t/D using the conventional method.

Ultrasonic beam transmitted from probes with incident angle $\alpha$ (relative to a normal line at a beam index of probe 1) can be geometrically indicated by ultrasonic beam with angle $\alpha_L$ (viewed on the longitudinal direction as shown in FIG. 4) and with angle $\alpha_t$ (viewed on transverse direction as shown in FIG. 5), (hereinafter, $\alpha_L$ called as longitudinal incident angle and $\alpha_t$ as transverse incident angle).

The relationship among the angles $\alpha$, $\alpha_L$ and $\alpha_t$ in that case can be expressed by the following equation.

$$\tan \alpha = \sqrt{\tan^2 \alpha_L + \tan^2 \alpha_t} \quad . \tag{1}$$

In the same manner, the ultrasonic beam propagating in the test material is also radiated onto the test material with the refraction angle $\theta$ having components $\theta_L$ and $\theta_t$ in the longitudinal and transverse directions, respectively.

The relationship among the angles $\theta$, $\theta_L$ and $\theta_t$ in that case can be expressed by the following equation in the same manner as in the case of equation (1):

$$\tan \theta = \sqrt{\tan^2 \theta_L + \tan^2 \theta_t} \quad . \tag{2}$$

Further relationships between the incidence angle and the refraction angle $\theta$ according to the laws of refraction of acoustic waves are expressed by the following equations:

$$\sin \theta = C_s/C_a \sin \alpha \tag{3}$$

$$\sin \theta_L = C_s/C_a \sin \alpha_L$$

$$\sin \theta_t = C_s/C_a \sin \alpha_t,$$

where $C_a$ represents the acoustic velocity of a compression wave in, for example, acryl, which is used for coupling ultrasonic waves into the test material from the transducer of the probe 1, and $C_s$ the acoustic velocity of shear waves in steel, the material of the test material. Generally, the shear wave acoustic velocity in steel is $C_s = 3240$ m/sec, and the compression wave acoustic velocity in acryl is $C_a = 2730$ m/sec.

The ultrasonic waves transmitted into the test material are caused to be incident on a longitudinal flaw of the inner surface at an incidence angle $\gamma$. In this case, the axial incidence angle $\gamma_L$ is the same as the axial refraction angle $\theta_L$.

However, as shown in FIG. 5, the transverse angular component $\gamma_t$ is geometrically larger than the transverse refraction angle $\theta_t$ by the angle $\beta$. The angle $\beta$, which represents the amount of increment in refraction angle when the ultrasonic beam impinges onto the inner surface flaw and generally referred to an as "incremental interior angle", is one of the limiting conditions in flaw detection with an ultrasonic angle beam technique when an inner surface londitudinal flaw in an ordinary steel pipe is detected from the outer surface of test material.

The following relationships are thus established:

$$\gamma_L = \theta_L \tag{4}$$

$$\gamma_t = \theta_t + \beta \tag{5}$$

$$\sin \gamma_t = \frac{\sin \theta_t}{(1 - 2t/D)} \quad . \tag{6}$$

The inner surface longitudinal flaw incidence angle in this case can be expressed by the following equation:

$$\tan \gamma = \sqrt{\tan^2 \gamma_L + \tan^2 \gamma_t} \quad .$$

Further, the inner surface longitudinal flaw incidence angle can be expressed as follows, using $\theta_L$ and $\theta_t$ from equations (4), (5) and (6):

$$\tan \gamma = \sqrt{\tan^2 \theta_L + \frac{(\sin^2 \theta_t)/(1 - 2t/D)^2}{1 - (\sin^2 \theta_t)/(1 - 2t/D)^2}} \quad . \tag{7}$$

It is necessary that $\theta_t$ satisfy equation (8). Unless $\theta_t$ satisfies equationn (8), the ultrasonic beam cannot reach the inner surface of the test material so that it becomes impossible to detect the inner surface longitudinal flaws:

$$\sin \theta_t \leq (1 - 2t/D) \tag{8}$$

With the foregoing conditions, it is made possible to select the refraction angle in the range of 35 to 70 degrees in the effective region G for detecting the flaw shown in FIG. 6, which is most suitable for flaw detection by ultrasonic angle beam with shear wave mode, with the longitudinal refraction angle $\theta_L$ and the transverse refraction angle $\theta_t$ being set in accordance with equations (2) and (7).

Thus, the ultrasonic beam is caused to impinge effectively onto the inner surface of the test material and be reflected by the inner surface longitudinal flaw toward the outer surface at a flaw reflection angle $\gamma$ (of which the longitudinal component is $\gamma_L$ and the transverse component is $\gamma_t$), reaching the outer surface at an outer surface incidence angle $\theta$ (of which the longitudinal component is $\theta_L$ and the transverse component is $\theta_t$). The ultrasonic beam reflected from the inner surface longitudinal flaw can be effectively received by the receiving probe by disposing the receiving probe in opposition to the transmitting probe, slanted by $\alpha_t$ on the transverse direction and by $\alpha_L$ on the longitudinal direction, as shown in FIG. 3, with the probe located at the position reached by the echo (which position is on the same axis as the transmitting probe 1, separated therefrom by the distance L in equation (9)).

$$L = D\{\cos \theta_t - \sqrt{(1 - 2t/D)^2 - \sin^2 \theta_t}\} \cdot \cos \theta_t \cdot \tan \theta_L. \tag{9}$$

If the ratio between the outer diameter of the test material and the width of the ultrasonic beam of the probe is relatively small, with the longitudinal refraction angle $\theta_L$ and transverse angle $\theta_t$ selected as described above, a part of the ultrasonic wave transmitted from the probe is directly reflected by the inner surface of the pipe only with a longitudinal component, and hence, in this case, a transmitted wave entering the receiving probe is generated. Moreover, it is necessary to select the longitudinal refraction angle $\theta_L$ and the transverse angle $\theta_t$ so as to cause an offset between the propagation path length $L_L$ of the transmitted wave and the path length $L_u$ of the wave reflected from the flaw. The values of $L_L$ and $L_u$ can be obtained from the following equations:

$$L_L = \frac{2t}{\cos \theta_L} \quad (10)$$

$$L_u = D \cdot \{\cos \theta_t - \sqrt{(1 - 2t/D)^2 - \sin^2 \theta_t}\}/\cos \theta_L \quad (11)$$

Table 1 shows an example of flaw detecting conditions established according to the present invention:

outer diameter (D) of the test material was varied within the range 2.5 to 35% in steps of 2.5%.

The calculated results prove that all values of the refraction angle $\theta$ and the inner surface longitudinal flaw incidence angle fall within the range 35 to 70 degrees, which is the effective range according to the present invention (for t/D ≦ 35%). This means that the effective range G according to the present invention (indicated in FIG. 6) provides a larger echo transmittance than the conventional method, making it possible to perform flaw detection with a higher sensitivity and reliability.

Figure 7:
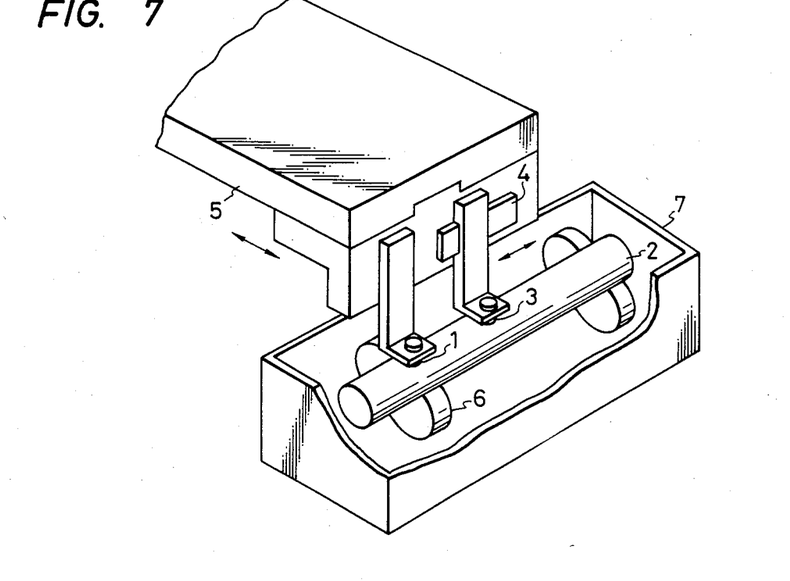
FIG. 7 is a diagram showing the external appearance of an apparatus used for practicing the present invention.

FIG. 7 depicts an example of an apparatus for detecting flaws in a longitudinal test material. Reference numerals 1 to 3 designate the same parts as in FIG. 3. Reference numeral 4 designates a positioning jig for adjusting the distance between the transmitting probe 1 and the receiving probe 3; 5 is a transverse incidence angle adjusting mechanism which carries the transmitting probe 1, the receiving probe 3, and the positioning jig 4, and which is movable perpendicularly to the longitudinal direction of the test material 2 to thereby adjust the transverse incidence angle; 6 a roller for rotating the test material; and 7 a water tank housing mem-

TABLE 1

| t/D (%) | | Circumferential Refraction Angle $\theta_t$ (Deg) | | | | | | | | | | |
|---|---|---|---|---|---|---|---|---|---|---|---|---|
| | | 7.5 | 10.0 | 12.5 | 15.0 | 17.5 | 20.0 | 22.5 | 25.0 | 27.5 | 30.0 | 32.5 | 35.0 |
| 20.0 | $\theta$ | 45.2 | 45.4 | 45.7 | 46.0 | 46.4 | 46.8 | 47.3 | 47.8 | 48.4 | 49.1 | 49.9 | 50.7 |
| | $\gamma$ | 45.7 | 46.3 | 47.0 | 47.9 | 49.1 | 50.6 | 52.8 | 54.6 | 57.4 | 61.1 | 66.0 | 73.6 |
| | L | 24.1 | 24.3 | 24.4 | 24.6 | 24.9 | 25.2 | 25.6 | 26.1 | 26.8 | 27.8 | 29.2 | 31.6 |
| | ΔBL | 0.5 | 0.9 | 1.4 | 2.1 | 2.9 | 4.0 | 5.2 | 6.8 | 8.8 | 11.7 | 15.0 | 20.6 |
| 22.5 | $\theta$ | 45.2 | 45.4 | 45.7 | 48.0 | 46.4 | 48.8 | 47.3 | 47.8 | 48.4 | 49.1 | 49.9 | — |
| | $\gamma$ | 45.8 | 46.5 | 47.4 | 48.6 | 50.1 | 51.9 | 54.8 | 57.4 | 61.5 | 67.4 | 77.9 | — |
| | L | 27.2 | 27.4 | 27.6 | 27.9 | 28.2 | 28.7 | 29.3 | 30.1 | 31.3 | 33.1 | 36.7 | — |
| | ΔBL | 0.8 | 1.1 | 1.8 | 2.6 | 3.7 | 5.0 | 6.7 | 8.9 | 11.7 | 15.9 | 23.4 | — |
| 25.0 | $\theta$ | 46.2 | 45.4 | 45.7 | 46.0 | 46.4 | 46.8 | 47.3 | 47.8 | 48.4 | 49.1 | — | — |
| | $\gamma$ | 46.0 | 46.8 | 48.0 | 49.4 | 51.4 | 53.9 | 57.2 | 61.9 | 69.0 | 89.9 | — | — |
| | L | 30.3 | 30.5 | 30.8 | 31.2 | 31.7 | 32.4 | 33.4 | 34.8 | 37.0 | 45.0 | — | — |
| | ΔBL | 0.7 | 1.4 | 2.2 | 3.2 | 4.6 | 6.4 | 8.7 | 11.8 | 16.6 | 31.0 | — | — |
| 27.5 | $\theta$ | 45.2 | 45.4 | 45.7 | 46.0 | 46.4 | 48.8 | 47.3 | 47.8 | — | — | — | — |
| | $\gamma$ | 46.3 | 47.3 | 48.8 | 50.7 | 53.4 | 57.0 | 62.3 | 71.0 | — | — | — | — |
| | L | 33.4 | 33.7 | 34.1 | 34.6 | 35.4 | 36.5 | 38.1 | 40.9 | — | — | — | — |
| | ΔBL | 0.9 | 1.7 | 2.7 | 4.1 | 5.8 | 8.3 | 11.6 | 17.1 | — | — | — | — |
| 30.0 | $\theta$ | 45.2 | 45.4 | 45.7 | 46.0 | 46.4 | 46.8 | 47.3 | — | — | — | — | — |
| | $\gamma$ | 48.8 | 48.0 | 49.9 | 52.7 | 56.8 | 62.6 | 73.8 | — | — | — | — | — |
| | L | 36.5 | 36.9 | 37.5 | 38.3 | 39.5 | 41.3 | 44.4 | — | — | — | — | — |
| | ΔBL | 1.1 | 2.1 | 3.4 | 5.2 | 7.6 | 11.2 | 17.6 | — | — | — | — | — |
| 32.5 | $\theta$ | 45.2 | 45.4 | 45.7 | 46.0 | 46.4 | 46.8 | — | — | — | — | — | — |
| | $\gamma$ | 47.1 | 49.0 | 51.8 | 56.1 | 62.9 | 78.0 | — | — | — | — | — | — |
| | L | 39.7 | 40.2 | 41.1 | 42.3 | 44.3 | 48.8 | — | — | — | — | — | — |
| | ΔBL | 1.4 | 2.6 | 4.3 | 6.8 | 10.6 | 18.3 | — | — | — | — | — | — |
| 35.0 | $\theta$ | 45.2 | 45.4 | 45.7 | 46.0 | — | — | — | — | — | — | — | — |
| | $\gamma$ | 48.0 | 50.8 | 55.3 | 63.2 | — | — | — | — | — | — | — | — |
| | L | 42.9 | 43.7 | 45.0 | 47.2 | — | — | — | — | — | — | — | — |
| | ΔBL | 1.8 | 3.4 | 5.8 | 8.7 | — | — | — | — | — | — | — | — | t/D: ratio of wall thickness to outer diameter of test material
$\theta$: refraction angle (deg)
L: probe interval (mm)
$\gamma$: inner surface flaw incidence angle (deg)
difference in propagation distances: $\Delta BL = L_u - L_L$
outer diameter: D = 60 mm
longitudinal refraction angle: $\theta_L = 45.0$ deg The refraction angle $\theta$ was calculated using equation (2), the flaw incidence angle with equation (7), the distance L between the transmitting probe and the receiving probe by equation (9), and the difference between the transmitted and the received wave path lengths $\Delta BL = (L_u - L_L)$ with equations (10) and (11), under the conditions that the outer diameter D and the longitudinal refraction angle $\theta_L$ were fixed at 60 and 45 degrees, respectively, the transverse refraction angle $\theta_t$ was varied within the range of 7.5 to 35.0 degrees in steps of 2.5 degrees, and the ratio (t/D of wall thickness (t) to the bers 1 to 6 and containing water as a couplant for coupling ultrasonically between the probe and the test material.

In the thus-arranged device for detecting flaws in a thick wall steel pipe with ultrasonic angle beam, the longitudinal incidence angle $\alpha_L$ indicated in FIGS. 3 to 5 uses the inherent incidence angle of each of the transmitting probe 1 and the receiving probe 3. Accordingly, the longitudinal refraction angle $\theta_L$ can be determined by equation (3). The transverse incidence angle $\alpha_t$ is set with the adjusting mechanism 5.

Figure 8:
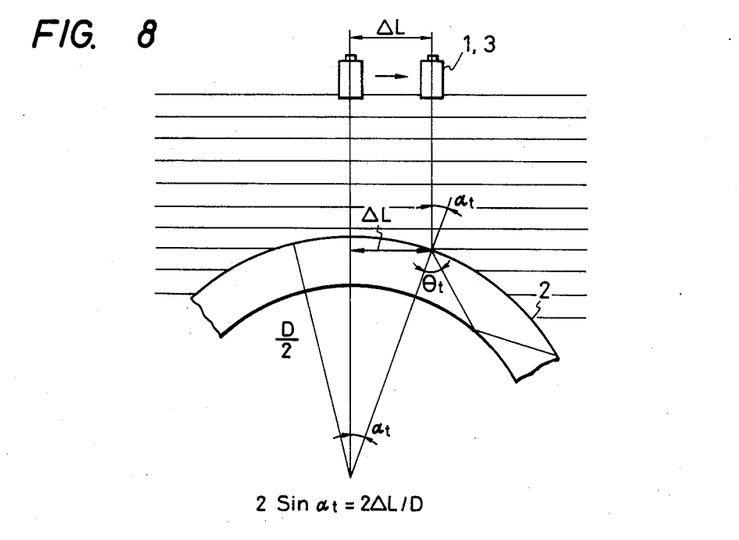
FIG. 8 is a diagram illustrating the principles of adjusting the circumferential incidence angle.

FIG. 8 is a diagram illustrating the adjustment of the transverse incidence angle $\alpha_t$.

The transverse incidence angle $\alpha_t$ can be geometrically calculated by the following equation using the amount of axis offset $\Delta L$ on transverse direction between the probes 1 and 3 and the test material 2 and the outer diameter D of the same one 2.

$$\sin \alpha_t = 2\Delta L/D. \tag{12}$$

the transverse refraction angle $\theta_t$ can be calculated from equation (3) using this value of $\alpha_t$. In this case, it is necessary to perform the calculations using the acoustic velocity in water (about 1500 m/sec) as the value of $C_a$.

The optimum transverse incidence angle is calculated from equations (2) and (7) using measured values of the outer diameter D and the wall thickness t of the test material and the amount of axis offset $\Delta L$ in the transverse direction established by the transverse incidence angle adjusting mechanism 5 is set in accordance with equation (12).

The distance L between beam index of the transmitting probe 1 and beam index of the receiving probe 3 is calculated from equation (9) and is set using the jig 4.

Flaw detection is performed over the whole circumference of the test material by rotating the test material with the turning rollers 6. If a computer-controlled adjusting mechanism is employed as the initial stage adjusting mechanism, needless to say, the measurements can more easily be performed.

It is a well-known fact that the echo level of a flaw varies depending on the ultrasonic beam incidence angle relative to the flaw, and in the conventional ultrasonic testing method for steel pipes, the incidence angle onto an inner surface longitudinal flaw is different from the incidence angle onto an outer surface longitudinal flaw. Hence, it has been almost impossible to detect longitudinal flaws of the inner and outer surfaces with the same sensitivity. However, according to the present invention, if a vertical probe for detecting exclusively flaws of the outer surface of a pipe and a transverse incidence angle adjusting mechanism are additionally provided for, the incidence angle can be adjusted in the same manner as the flaw incidence angle for the inner surface, and thus it is made possible to perform flaw detection with the same sensitivity and with a better S/N ratio for both the inner and outer surfaces of the pipes.

The above description relates to a case in which the present invention is used for detecting longitudinal flaws of the inner surface of a thick wall steel pipe. However, the present invention can be used for inspection of a steel pipe for which the ratio t/D of wall thickness (t) to outer diameter (D) is less while still detecting inner and outer surface longitudinal flaws with the same sensitivity. Further, the types of inner surface flaws which can be accurately detected using the inventive method include point-like flaws (Acoustically nondirectional flaws) and flaws extending perpendicular to the transmitted ultrasonic beam (which can be made perpendicular to the ultrasonic beam by adjusting the axial and circumferential angles so that an echo is returned to the probe 1). Also, the present invention can be used for classifying the types of flaws and for detecting slanted flaws, which have been conventionally difficult to detect.

As described above, the present invention has the effect that flaws can be detected with a higher sensitivity than in the case of the conventional method by causing a shear wave of an ultrasonic beam to impinge onto longitudinal flaws of the inner surface of a pipe at an angle within a range of 35 to 70 degrees, which is most suitable for performing flaw detection by shear wave, by slanting the probe in the longitudinal and transverse directions of the pipe.

Further, there is another effect that flaw detection is less affected by deformations in the inner and outer diameters of the pipe or by a rough outer surface because it is unnecessary to make the ultrasonic beam reflect from the outer surface of the pipe. Further, flaw detection of the inner and outer surfaces can be performed with the same sensitivity by combining an outer surface flaw detecting method using an outer surface flaw detecting probe having a refraction angle which is equal to the incidence angle onto the inner surface of the pipe.

We claim:

1. In a method of detecting longitudinal flaws in a thick wall steel pipe with an ultrasonic beam in which the flaw on an inner surface of a thick wall steel pipe being tested is detected by a shear wave of the ultrasonic beam using a transmitting probe (1) and a receiving probe (3), the improvement wherein said transmitting probe is disposed slantingly relative to longitudinal and transverse directions of said pipe so that the shear wave of an ultrasonic beam transmitted therefrom is incident onto said pipe at an oblique refraction angle and said transmitted wave impinges onto a longitudinal flaw on said inner surface of said pipe at an oblique incidence angle, and said receiving probe is disposed geometrically so as to receive ultrasonic waves reflected from said flaw of said inner surface; and wherein a transverse incidence angle $\gamma$ of said ultrasonic beam is determined in accordance with:

$$\tan \gamma = \sqrt{\tan^2 \theta_L + \frac{(\sin^2 \theta_t)/(1 - 2t/D)^2}{1 - (\sin^2 \theta_t)/(1 - 2t/D)^2}},$$

where $\theta_L$ is an angular component of said refraction angle, $\theta_t$ is a transverse component of said refraction angle in said pipe, t is a wall thickness of said pipe, and D is an outer diameter of said pipe.

2. The method of detecting flaws in a thick wall steel pipe according to claim 1, wherein the transmitted shear wave of an ultrasonic beam is slantingly incident only in a transverse direction onto said steel pipe from an outer surface thereof, such that a refraction angle thereof is made equal to said incidence angle onto said inner surface flaw, whereby inner surface flaws on said pipe are detected by said shear wave.

3. The method of detecting flaws in a thick wall steel pipe according to claim 1 wherein an amount of axis offset $\Delta L$ in the transverse direction between said transmitting and receiving probes is determined in accordance with: where $\alpha_t$ is an incidence angle of said transmitted beam from said transmitting probe viewed in a transverse direction.

4. In a method of detecting longitudinal flaws in a thick wall steel pipe with an ultrasonic beam in which the flaw on an inner surface of a thick wall steel pipe being tested is detected by a shear wave of the ultrasonic beam using a transmitting probe (1) and a receiving probe (3), the improvement wherein said transmitting probe is disposed slantingly relative to longitudinal and transverse directions of said pipe so that the shear wave of an ultrasonic beam transmitted therefrom is incident onto said pipe at an oblique refraction angle within a range of 35 to 70 degrees and said transmitted wave impinges onto a longitudinal flaw on said inner surface of said pipe at an oblique incidence angle within a range of 35 to 70 degrees, and said receiving probe is disposed geometrically so as to receive ultrasonic waves reflected from said flaw of said inner surface; and wherein a transverse incidence angle $\gamma$ of said ultrasonic beam is determined in accordance with:

$$\tan \gamma = \sqrt{\tan^2 \theta_L + \frac{(\sin^2 \theta_t)/(1 - 2t/D)^2}{1 - (\sin^2 \theta_t)/(1 - 2t/D)^2}},$$

where $\theta_L$ is an angular component of said refraction angle, $\theta_t$ is a transverse component of said refraction angle in said pipe, t is a wall thickness of said pipe, and D is an outer diameter of said pipe.

5. The method of detecting flaws in a thick wall steel pipe according to claim 4, wherein a transmitted shear wave of an ultrasonic beam is slantingly incident only in a transverse direction onto said steel pipe from an outer surface thereof, such that a refraction angle thereof is made equal to said incidence angle onto said inner surface flaw, whereby inner surface flaws on said pipe are detected by said shear wave.

6. The method of detecting flaws in a thick wall steel pipe according to claim 4, wherein an amount of axis offset $\Delta_L$ in the transverse direction between said trasmitting and receiving probes is determined in accordance with:

$$\sin \alpha_t = 2\Delta L/D,$$

where $\alpha_t$ is an incidence angle of said transmitted beam from said transmitting probe viewed in a transverse direction.

* * * * *